United States Patent [19]

Epp et al.

[11] Patent Number: 4,952,502

[45] Date of Patent: Aug. 28, 1990

[54] CARBOMYCIN BIOSYNTHETIC GENE, DESIGNATED CARG, FOR USE IN STREPTOMYCES AND OTHER ORGANISMS

[75] Inventors: Janet K. Epp; Brigitte E. Schoner, both of Indianapolis, Ind.

[73] Assignee: Eli Lilly and Company, Indianapolis, Ind.

[21] Appl. No.: 17,660

[22] Filed: Feb. 24, 1987

[51] Int. Cl.$^5$ .................. C12P 19/62; C12P 19/34; C12N 1/21; C12N 15/52

[52] U.S. Cl. ............................... 435/76; 435/91; 435/172.1; 435/172.3; 435/252.33; 435/252.35; 435/320; 435/886; 536/27; 935/9; 935/22; 935/38; 935/61; 935/73; 935/75

[58] Field of Search ............ 435/76, 91, 172.1, 172.3, 435/252.33, 252.35, 256, 320, 886; 536/27; 935/19, 23, 27, 38, 55, 60

[56] References Cited

U.S. PATENT DOCUMENTS

| | | | |
|---|---|---|---|
| 2,902,412 | 9/1959 | Pagano et al. | 435/76 |
| 4,904,591 | 2/1990 | Epp et al. | 435/172.3 |

OTHER PUBLICATIONS

Kirby et al., 1975, Nature 254(5497):265.
Kirby and Hopwood, 1977, J. Gen. Microbiol. 98:239.
Gil and Hopwood, 1983, Gene 25:119.
Feitelson et al., 1983 Mol. Gen. Genet. 190:394–398.
Hopwood et al., 1983, Trends in Biotech. 1(2):42–48.
Chater and Bruton. 1983, Gene 26:67–78.
Vourhakis and Elander, 1983, Science 219:703.
Rhodes et al., 1984, Biochem. Soc. Trans. 12:586.
Jones and Hopwood, 1984, J. Biol. Chem. 259(22):14151.
Malpartida and Hopwood, 1984, Nature 309:462.
Bailey et al., 1984, Bio/Technology Sep.:808–811.
Hopwood et al., 1985, Nature 314:642–644.
DeMain, 1985, Nature 314:577–578.
Distler et al., 1985, FEMS Microbiol. Letters 30:151–154.
Fishman et al., 3/86, Poster Session at the American Society of Microbiologists (ASM) Meeting in Washington, D.C.
Stanzak et al., 1986, Bio/Technology 4:229.
Fayerman, 1986, Bio/Technology 4:786.
Epp and Schoner, Mar. 1987, Poster Session at the UCLA Symposium on Molecular Genetics of Streptomyces.
Thompson et al., 1982, J. Bacteriol. 151:668–677.
Thompson et al., 1982, J. Bacteriol. 151:678–685.

Primary Examiner—Richard A. Schwartz
Assistant Examiner—Richard C. Peet
Attorney, Agent, or Firm—Douglas K. Norman; Leroy Whitaker

[57] ABSTRACT

The carG gene of *Streptomyces thermotolerans* has been isolated and used to construct recombinant DNA expression vectors. The carG gene encodes the activities required for the biosynthesis of the 16-member cyclic lactone of carbomycin. The carG gene can be used not only to construct recombinant cells with an increased ability to produce carbomycin but also to construct recombinant cells with the ability to produce novel antibiotic compounds.

23 Claims, 3 Drawing Sheets

Figure 1
Restriction Site and Function Map of Plasmid pOJ171 (~45 kb)

Figure 2
Restriction Site and Function Map
of Plasmid pOJ160
(~7 kb)

Figure 3
Restriction Site and Function Map of Plasmid pOJ325 (~21 kb)

CARBOMYCIN BIOSYNTHETIC GENE, DESIGNATED CARG, FOR USE IN STREPTOMYCES AND OTHER ORGANISMS

SUMMARY OF THE INVENTION

The present invention comprises a novel carbomycin biosynthetic gene, designated carG, a method for using the carG gene, recombinant DNA cloning vectors that comprise the novel gene, and transformants containing the novel vectors. *Streptomyces thermotolerans* (ATCC 11416) produces carbomycin, a macrolide antibiotic consisting of a 16-member cyclic lactone and two sugar residues. The antibiotic activity of carbomycin like that of other macrolides, is due to inhibition of protein synthesis by a mechanism that involves the binding of carbomycin to the ribosome. The carGgene encodes the activities required to produce the 16-member cyclic lactone of carbomycin.

The present invention provides carbomycin biosynthetic gene expression vectors for use in Streptomyces has a and other host cells. The development and exploitation of recombinant DNA technology in has Streptomyces been driven by the desire to improve the antibiotic-producing ability of this industrially important organism, not only to increase antibiotic yield, but also to produce novel antibiotics. This development has been somewhat retarded by the low number of antibiotic biosynthetic genes presently available for use in modifying Streptomyces by recombinant DNA technology. The present invention is useful and especially important in that it expands the number of antibiotic biosynthetic genes suitable for such use.

The vectors of the present invention are particularly useful, because the vectors can be introduced into and selected for in a variety of Streptomyces cells. Streptomyces provides over half of the clinically important antibiotics and thus is a commercially significant group. The present invention provides new and useful vectors and methods not only for this industrially important group but also for other antibiotic-producing organisms and allows for increasing the yield of carbomycin in fermentations and also for producing new antibiotics and antibiotic derivatives.

For purposes of the present invention, as disclosed and claimed herein, the following terms are defined below.

AmR - the apramycin resistance-conferring gene.

Antibiotic - a substance produced by a microorganism which, either naturally or with limited modification, will inhibit the growth of or kill another microorganism or eukaryotic cell.

Antibiotic Biosynthetic Gene - a DNA segment that encodes one or more activities that are necessary in the biochemical process of converting primary metabolites into antibiotics.

Antibiotic Biosynthetic Pathway - the entire set of antibiotic biosynthetic genes necessary for the process of converting primary metabolites into antibiotics.

Antibiotic-Producing Organism - any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

Antibiotic Resistance-Conferring Gene - a DNA segment that encodes an enzymatic or other activity that confers resistance to an antibiotic.

ApR - the ampicillin resistance-conferring gene.

Bifunctional Cloning Shuttle Vector - a recombinant DNA cloning vector that can replicate and/or integrate into organisms of two different taxa.

Cloning - the process of incorporating a segment of DNA into a recombinant DNA cloning vector and transforming a host cell with the recombinant DNA.

carA - a carbomycin resistance-conferring gene of type A.

carB - a carbomycin resistance-conferring gene of type B.

carG - a DNA sequence that comprises one or more genes that encode the activities required to form the 16-member cyclic lactone of carbomycin.

cos - the lambda cohesive end sequence.

Cosmid - a recombinant DNA cloning vector which not only can replicate in a host cell in the same manner as a plasmid but also can be packaged into phage heads.

Gene - A DNA sequence that comprises a promoter and coding sequence positioned so that the promoter drives transcription of the coding sequence.

Genetic Library - a set of recombinant DNA cloning vectors into which segments of DNA, comprising substantially all of the DNA of a particular organism, have been cloned.

Hybridization - the process of annealing two single-stranded DNA molecules to form a double-stranded DNA molecule, which may or may not be completely base-paired.

NmR - the neomycin resistance-conferring gene.

ori - a plasmid origin of replication.

Phasmid—a recombinant DNA vector that may act as a phage or as a plasmid.

Recombinant DNA Cloning Vector - any autonomously replicating or integrating agent, including, but not limited to, plasmids, comprising a DNA molecule to which one or more additional DNA molecules can be or have been added.

Restriction Fragment - any linear DNA molecule generated by the action of one or more restriction enzymes.

rRNA - ribosomal ribonucleic acid.

Sensitive Host Cell - a host cell that cannot grow in the presence of a given antibiotic without a DNA segment that confers resistance thereto.

TcR - the tetracycline-resistant phenotype or gene conferring same.

Transductant - a recipient host cell that has undergone transformation by recombinant phage infection.

Transformant - a recipient host cell that has undergone transformation.

Transformation - the introduction of DNA into a recipient host cell that changes the genotype and results in a change in the recipient cell.

tsrR - the thiostrepton-resistant phenotype or gene conferring same.

BRIEF DESCRIPTION OF THE FIGURES

The figures described below are drawn to scale; however, observed restriction fragment size may vary somewhat from calculated size based on map distances. For some restriction enzymes, such as MboI, only certain cut sites are shown for convenience.

DETAILED DESCRIPTION OF THE INVENTION

Figure 1:
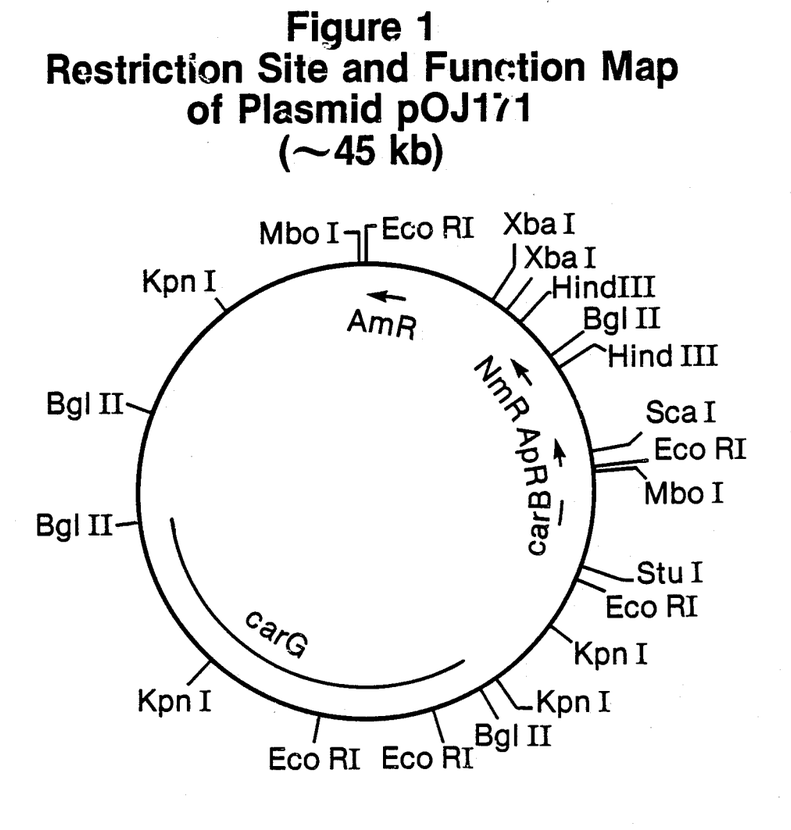
FIG. 1 is a restriction site and function map of plasmid pOJ171.

The present invention comprises a novel carbomycin biosynthetic gene, designated carG, that can be used to increase antibiotic yield and to produce new antibiotics. The carG gene is useful in a method for increasing the carbomycin-producing ability of an organism that comprises transforming the organism with a recombinant DNA vector that codes for expression of the carG gene product and culturing the transformed cell under conditions suitable for producing carbomycin. The carG gene can be isolated from plasmid pOJ171 on an ~14.0 kb BglII restriction fragment; plasmid pOJ171 can be isolated from *E. coli* K12 SF8/pOJ171, a strain deposited and made part of the permanent culture collection of the Agricultural Research Serviee, Northern Regional Research Center (NRRL), Peoria, Ill. 61604, under the accession number NRRL B-18169. A restriction site and function map of plasmid pOJ171 is presented in FIG. 1 of the accompanying drawings. Plasmid pOJ171 can be isolated from *E. coli* K12 SF8/pOJ171 in substantial accordance with the procedure described in Example 1.

Plasmid pOJ171 serves as useful starting material for the construction of other vectors that contain the carG carbomycin biosynthetic gene. For example, the ~14.0 kb BglII, carbomycin biosynthetic gene-containing restriction fragment of plasmid pOJ171 was isolated and inserted into BglII-digested plasmid pOJ160 (NRRL B-18088) to yield plasmids pOJ325 and pOJ325A, which differ only with respect to the orientation of the ~14.0 kb BglII, carbomycin biosynthetic-containing restriction fragment. The construction protocol for plasmids pOJ325 and pOJ325A is given in Example 2; a restriction site and function map of plasmid pOJ325 is presented in FIG. 3 of the accompanying drawings.

The carG-containing, ~14 kb BglII restriction fragment of the present invention may actually comprise more than one gene. The activity of the carG gene is best understood by defining the mutation which the carG gene complements. Certain mutants of *Streptomyces thermotolerans*, such as NRRL 15270, described in U.S. Pat. No. 4,522,919, do not produce carbomycin or carbomycin-related compounds unless supplemented with the 16-member cyclic lactone of carbomycin or similar antibiotics. The carG gene of the present invention encodes the enzymatic activities required to allow an organism such as NRRL 15270 to produce carbomycin without supplying the 16-member cyclic lactone. Similarly, when the carG gene of the present invention is introduced into other strains of macrolide-producing *Streptomyces*, these transformed organisms produce a variety of hybrid antibiotics.

The carG gene was isolated from a carbomycin-producing strain of *Streptomyces thermotolerans* (ATCC 11416). Thus, genomic DNA of *S. thermotolerans* was partially digested with restriction enzyme MboI, and the resulting DNA was inserted into HpaI-BamHI-digested cosmid pKC462A to yield a number of carG-containing plasmids, including plasmid pOJ171. Plasmid pKC462A (NRRL B-15973) is a cosmid shuttle vector of the type described in U.S. patent application Ser. No. 842,102, filed Mar. 20, 1986, attorney docket No. X-6422B.

The vectors of the present invention can be used to transform a variety of organisms to increase the carbomycin-producing ability of the organism or to enable the organism to synthesize the 16-member cyclic lactone of carbomycin, a useful intermediate in antibiotic biosynthesis. In addition, the carG gene can be used to transform a variety of antibiotic-producing organisms, particularly macrolide antibiotic-producing organisms, for purposes of making novel antibiotics. The carG gene itself can be reconstructed using recombinant DNA techniques for purposes of producing the carG gene product in non-Streptomyces species. The following Tables present a representative sampling of various antibiotic-producing organisms in which the carG gene can be used either to produce a novel antibiotic or to increase antibiotic production.

TABLE I

Ansamycin Antibiotic-Producing Organisms

| Organism | Antibiotic |
|---|---|
| *Micromonospora* various species | various ansamycins |
| *Nocardia mediterranei* | rifamycin |
| *Streptomyces collinus* | ansatrienes and napthomycins |
| *diastochromogenes* | ansatrienes and napthomycins |
| *galbus* subsp. *griseosporeus* | napthomycin B |
| *hygroscopicus* | herbimycin |
| *hygroscopicus* var. *geldanus* var. *nova* | geldamycin |
| *nigellus* | 21-hydroxy-25-demethyl 25-methylthioproto-streptovaricin |
| *rishiriensis* | mycotrienes |
| sp. E/784 | actamycin and mycotrienes |
| sp. E88 | mycotrienes |
| *spectabilis* | streptovaricins |
| *tolypophorous* | tolypomycin |

TABLE II

Anthracycline and Quinone Antibiotic-Producing Organisms

| Organism | Antibiotic |
|---|---|
| *Streptomyces caespitosus* | mitomycins A, B, and C |
| *coelicolor* | actinorhodin |
| *coeruleorubidicus* | daunomycin |
| *cyaneus* | ditrisarubicin |
| *flavogriseus* | cyanocycline A |
| *galilaeus* | aclacinomycin A, auramycins, and sulfurmycins |
| *lusitanus* | napthyridinomycin |
| *peuceticus* | daunomycin and adriamycin |
| *violochromogenes* | arugomycin |

TABLE III

Macrolide, Lincosamide, and Streptogramin Antibiotic-Producing Organisms

| Organism | Antibiotic |
|---|---|
| *Micromonospora rosaria* | rosaramicin |
| *Streptomyces albireticuli* | carbomycin |
| *albogriseolus* | mikonomycin |
| *albus* | albomycetin |
| *albus* var. *coilmyceticus* | coleimycin |

TABLE III-continued

Macrolide, Lincosamide, and Streptogramin Antibiotic-Producing Organisms

| Organism | Antibiotic |
|---|---|
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| Streptomyces griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A$_3$ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A$_3$ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE IV

Miscellaneous Antibiotic-Producing Streptomyces

| Antibiotic Type | Streptomyces Species | Antibiotic |
|---|---|---|
| cyclopentane ring-containing | coelicolor | methylenomycin A |
| | erythrochromogenes | sarkomycin |
| | kasugaensis | aureothricin and thiolutin |
| | violaceoruber | methylenomycin A |
| polyenes | griseus | candicidin |
| | nodosus | amphotericin B |
| | noursei | nystatin |
| tetracyclines | aureofaciens | tetracycline, chlortetracycline, demethyltetracycline, and demethylchlortetracycline |
| | rimosus | oxytetracycline |

TABLE V

Polyether Antibiotic-Producing Organism

| Organism | Antibiotic |
|---|---|
| Actinomadura various species | various polyethers |
| oligosporus | A80190 |
| Dactylosporangium various species | various polyethers |
| Nocardia various species | various polyethers |
| Streptomyces albus | A204, A28695A and B, and salinomycin |
| aureofaciens | narasin |
| bobili | A80438 |
| cacaoi var. asoensis | lysocellin |
| chartreusis | A23187 |
| cinnamonensis | monensin |
| conglobatus | ionomycin |
| eurocidicus var. asterocidicus | laidlomycin |
| flaveolus | CP38936 |
| gallinarius | RP 30504 |
| griseus | grisorixin |
| hygroscopicus | A218, emericid, DE3936, A120A, A28695A and B, etheromycin, and dianemycin |
| lasaliensis | lasalocid |
| longwoodensis | lysocellin |
| mutabilis | S-11743a |
| pactum | A80438 |
| ribosidificus | lonomycin |
| violaceoniger | nigericin |
| Streptoverticillium various species | various polyethers |

Illustrative vectors of the present invention were introduced into *Streptomyces thermotolerans* NRRL 15270 for purposes of exemplifying the use of the carG gene to increase the carbomycin-producing ability of an organism. *S. thermotolerans* NRRL 15270 was derived from *S. thermotolerans* ATCC 11416 by mutagenesis as described in U.S. Pat. No. 4,552,919. NRRL 15270 does not produce carbomycin because of a deletion in the carG region of the chromosome. This deletion is about 6 kb in size, which indicates that the ~14 kb BglII carG-containing restriction fragment of the present invention could be reduced in size yet still confer the carG activity. When vectors containing the carG gene of the present invention are used to transform NRRL 15270, however, the resulting transformants produce more carbomycin than *S. thermotolerans* ATCC 11416. The transformation of *S. thermotolerans* NRRL 15270 and the comparison of the resulting transformants with

*S. thermotolerans* ATCC 11416 is described in Examples 3 and 4, below.

The carG gene functions particularly well in *Streptomyces thermotolerans*. Yet even if the original carG gene failed to express in a given organism, such as *E. coli*, because, for example, the Streptomyces promoter failed to function in that organism, the carG coding sequence of the present invention could be ligated to a DNA containing an appropriate promoter and ribosome-binding site to achieve expression of the carG gene in the host of choice.

Plasmid pOJ171 contains the carG gene: (1) a promoter that directs transcription of the protein-coding sequence; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. The DNA sequence of the carG gene reveals the location of the carG coding sequence and thus allows one to position other promoters, for example, the trp, lpp, and lac promoters of *E. coli*, the hybrid tac promoter, and the veg promoter of Bacillus, in reading phase with the carG coding sequence. By choosing the proper promoter, one can construct vectors that drive expression of the carG gene product in any host cell. The promoter of the carG gene is useful in its own right. The promoter and other regulatory elements of the carG gene can be linked to the coding sequence of a non-carbomycin antibiotic biosynthetic gene to prepare a hybrid antibiotic pathway gene that functions in other Streptomyces species to yield a hybrid antibiotics. Thus, the individual elements of the gene on the plasmids described herein comprise important components of the present invention.

Those skilled in the art will recognize that the carG sequence deposited under accession number NRRL B-18169 can be used to prepare DNA probes for use in obtaining other biosynthetic gene-containing DNA segments, especially segments encoding macrolide biosynthetic genes. In addition, due to the diversity of *Streptomyces thermotolerans* strains both in nature and also in the laboratory, there will be a variety of allelic variants of the carG gene that can be readily isolated given the carG gene-containing compounds of this invention. These allelic variants, which encode gene products with an amino acid residue sequence that differs from that of the carG gene product in only a few residues, are functionally equivalent to the carG gene of the present invention.

A variety of known Streptomyces replicons can be used in conjunction with the carG gene to construct expression vectors of the present invention. Table VI is an illustrative, but not comprehensive, listing of Streptomyces plasmids from which Streptomyces replicons can be obtained. Those skilled in the art recognize that, so long as the replicon function is not disrupted, all or part of the plasmids can be used to construct vectors that contain the carG gene of the present invention. The plasmid-containing host and depository accession number are also listed in Table VI.

TABLE VI

| Plasmid | Streptomyces Plasmids Host | Accession Number |
|---|---|---|
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

Restriction fragments used to construct vectors illustrative of the present invention can be conventionally modified to facilitate ligation. For example, molecular linkers can be provided to a particular carG biosynthetic gene-containing restriction fragment or to DNA comprising vector replication or integration functions. Thus, specific sites for subsequent ligation can be conveniently constructed. In addition, the various carG biosynthetic gene-containing restriction fragments, origin of replication, or sequences that provide for chromosomal integration of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that a given carG biosynthetic gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular carG gene-containing restriction fragment.

Of course, the carG gene can be used to construct vectors other than plasmids. Phage ØC31 is a well-known Streptomyces phage that is an excellent source of starting material for constructing integrative carbomycin resistance-conferring vectors that further exemplify the present invention. A derivative of phage ØC31, phasmid pKC331, is especially preferred for constructing such integrating vectors and can be obtained from *E. coli* K12 BE447/pKC331 (NRRL B-15828). ØC31-type phages are integrative vectors and can be readily modified to incorporate the carG gene and thus confer carG activity to Streptomyces. Even plasmids that contain a replicon that provides for extrachromosomal maintenance of the plasmid sometimes integrate into the genome of the host cell, usually with concomitant deletion of the replicon sequences. The present invention thus is not limited by the type of vector used to introduce the carG gene into the target host cell nor by the location of the carG gene once introduction has occurred.

The vectors of the present invention comprise a Streptomyces replicon and a carG gene-containing restriction fragment. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pUC8, pUC18, pUC19, pBR322, pACYC184, pBR325, pBR328, and the like is highly advantageous and adds to the general utility of the present illustrative vectors.

*Streptomyces thermotolerans* contains two carbomycin resistance-conferring genes, designated carA and carB. These two carbomycin resistance genes may act in concert to cause high-level resistance in Streptomyces thermotolerans. The carA gene is disclosed and claimed in, Epp et al., U.S. patent application Ser. No. 901,240, attorney docket No. X-6935, filed Aug. 28, 1986, while the carB gene is disclosed and claimed in Epp et al., U.S. patent application Ser. No. 901,334, attorney docket No. X-7135, filed Aug. 28, 1986. The present invention also comprises vectors that contain the carG gene and either or both of the carA and carB genes. Plasmid pOJ171, for example, comprises both the carG and carB genes.

The cloning vectors and transformants of the present invention provide for the cloning of genes to improve yields of various products that are currently produced in Streptomyces and related cells. Examples of such products include, but are not limited to, Carbomycin Streptomycin, Tylosin, Cephalosporins, Actaplanin, Narasin, Monensin, Tobramycin, Erythromycin, and the like. The present invention also provides selectable vectors that are useful for cloning, characterizing, and reconstructing a variety of useful DNA sequences.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pOJ171

A. Culture of *E. coli* K12 SF8/pOJ171

Plasmid pOJ171 can be obtained from the Northern Regional Research Center in *E. coli* K12 SF8 under the accession number NRRL B-18169. The lyophils of *E. coli* K12 SF8/pOJ171 are plated onto L-agar plates (10 g of Bacto-tryptone, 10 g of NaCl, 5 g of Bacto-Yeast Extract, and 15 g of agar per liter) containing 200 μg/ml apramycin to obtain a single colony isolate of the strain. This colony is used to inoculate about 500 ml of L broth (L agar without agar) containing 200 μg/ml apramycin, and the resulting culture is incubated at 37° C. with aeration until the cells reach stationary phase.

Plasmid DNA was obtained from the cells to use in construction of plasmid pOJ325 in accordance with the following procedure, which is adapted from Maniatis et al., 1982, *Molecular Cloning* (Cold Spring Harbor Laboratory). This same procedure was used, but on a smaller scale and with the ultracentrifugation steps replaced with phenol followed by chloroform extractions, to prepare the plasmid DNA used to identify the *E. coli* K12 RR1ΔM15/pOJ325 transformants.

About 500 ml of stationary-phase *E. coli* /pOJ171 cells are harvested by centrifugation at 4000Xg for 10 minutes at 4° C., and the supernatant is discarded. The cell pellet is washed in 100 ml of ice-cold STE buffer (0.1 M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 1 mg/ml lysozyme and is left at room temperature for 10 minutes. Twenty ml of Solution 2 (0.2 N NaOH and 1% SDS) are then added to the lysozyme-treated cells, and the solution is gently mixed by inversion. The mixture is incubated on ice for 10 minutes.

Fifteen ml of ice-cold, 3M sodium acetate, pH=4.8, are added to the lysed-cell mixture, and the solution is mixed by inversion. The solution is incubated on ice for 60 minutes. The 3M sodium acetate solution is prepared by mixing equal volumes of 3M acetic acid and 3M sodium acetate.

The lysed cell mixture is centrifuged in a Beckman SW27 rotor (or its equivalent) at 20,000 rpm for 20 minutes at 4° C. About 36 ml of supernatant are recovered, and 2.5 volumes of ethanol are added, mixed, and the resulting solution left on ice for 15 minutes. The plasmid DNA is collected by centrifugation at 12,000Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer (10 mM Tris-HCl, pH=8.0, and 1 mM EDTA).

Eight grams of CsCl are added to the DNA solution. About 0.8 ml of a 10 mg/ml solution of ethidium bromide in water are added for each 10 ml of CsCl-DNA solution. The final density of the solution is about 0.761 g/ml, and the ethidium bromide concentration is about 800 μg/ml. The solution is transferred to a Beckman Type 50 centrifuge tube, filled to the top with TE buffer containing 0.761 g of CsCl per ml, sealed, and centrifuged at 45,000 rpm for 24 hours at 20° C. After centrifugation, two bands of DNA are visible in ordinary light and become even more prominent in UV light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 0.5 mg of plasmid pOJ171 DNA can be obtained by this procedure. A restriction site and function map of plasmid pOJ171 is presented in FIG. 1 of the accompanying drawings.

EXAMPLE 2

Construction of Plasmid pOJ325 and pOJ325A

A. Isolation of Plasmid pOJ160

Plasmid pOJ160 can be obtained from the Northern Regional Research Center in *E. coli* K12 JM109 under the accession number NRRL B-18088. The lyophils of *E. coli* K12 JM109/pOJ160 are plated onto L-agar plates (10 g of Bacto-tryptone, 10 g of NaCl, 5 g of Bacto-Yeast Extract, and 15 g of agar per liter) containing 200 µg/ml apramycin to obtain a single colony isolate of the strain. This colony is used to inoculate about 500 ml of L broth (L agar without agar) containing 200 µg/ml apramycin, and the resulting culture is incubated at 37° C. with aeration until the cells reach stationary phase.

Figure 2:
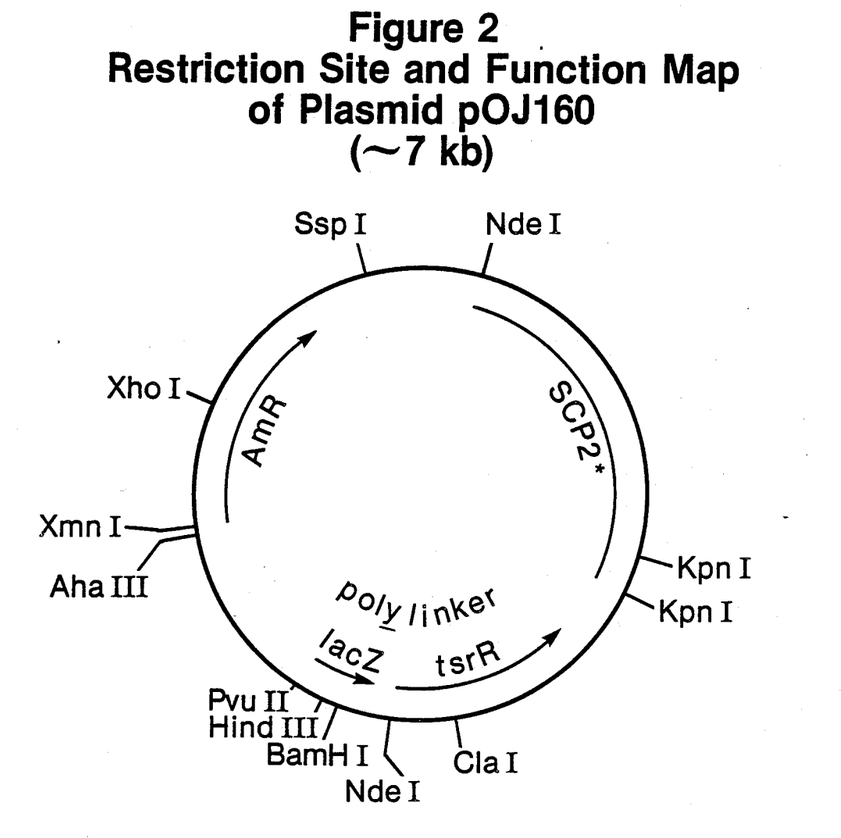
FIG. 2 is a restriction site and function map of plasmid pOJ160.

Plasmid DNA was obtained from the cells to use in construction of plasmid pOJ325 in accordance with the procedure set forth in Example 1, above. About 0.5 mg of plasmid pOJ160 DNA can be obtained by this procedure. A restriction site and function map of plasmid pOJ160 is presented in FIG. 2 of the accompanying drawings.

B. Final Construction of Plasmid pOJ325

About 10 µg (10 µl) of plasmid pOJ160 DNA were added to 2 µl of 10X BamHI buffer (60 mM Tris-HCl, pH=7.9; 1.5 M NaCl; 1 mg/ml BSA; and 60 mM MgCl$_2$), 6 µl of H$_2$O, and 2 µl (~30 units; unit definitions herein correspond to those of New England Biolabs, 32 Tozer Road, Beverly, Mass. 01915-9990, unless otherwise indicated) of restriction enzyme BamHI. The resulting reaction was incubated at 37° C. for two hours. The BamHI-digested plasmid pOJ160 DNA was collected by adjusting the sodium acetate (NaOAc) concentration of the reaction mixture to 0.30M, adding 2.5 volumes of ethanol, chilling the reaction mixture to −70° C., and centrifuging to pellet the precipitated DNA. The pellet of BamHI-digested plasmid pOJ160 DNA was resuspended in 400 µl of TE buffer (10 mM Tris-HCl, pH=8.0, and 1 mM EDTA). About 1 µl (0.1 unit) of bacterial alkaline phosphatase (International Biotechnology, Inc., P.O. Box 1565, New Haven, Conn. 06506) was added to the DNA solution, and the reaction was incubated at 65° C. for 1 hour. The reaction mixture was extracted with 400 µl of a 1:1 solution of phenol:chloroform and then extracted with 400 µl of chloroform. The BamHI-digested, dephosphorylated plasmid pOJ160 DNA was collected by ethanol precipitation and centrifugation as described above, and the DNA pellet was resuspended in 10 µl of TE buffer.

About 10 µg of plasmid pOJ171 in 100 µg of TE buffer were added to 13 µg of 10X BglII buffer (1.0M NaCl; 100 mM Tris-HCl pH=7.4; 100 mM MgCl$_2$; 100 mM 2-mercaptoethanol; and 1 mg/ml BSA), 13 µg of H$_2$0 and 4 µg (~60 units) of restriction enzyme BglII. The resulting reaction was incubated at 37° C. for 2 hours. The reaction mixture was extracted, and the DNA was collected as described above. The DNA pellet was dissolved in 50 µg of TE buffer and contained ~2.5 µg of the desired ~14 kb BglII restriction fragment of plasmid pOJ171.

The BamHI-digested, dephosphorylated plasmid pOJ160 DNA (1 µl) was added to 10 µg (~0.5 µg) of the BglII-digested plasmid pOJ171 DNA, 2 µg of 10X ligase buffer (660 mM Tris-HCl, pH=8; 66 mM MgCl$_2$; 10 mM dithiothreitol (DTT); and 10 mM ATP), and 6 µg of H20. About 1 µg (~100 units) of T4 DNA ligase was added to the solution of DNA, and the resulting reaction was incubated at 15° C. overnight (~16 hours). The ligated DNA contained the desired plasmid pOJ325; a restriction site and function map of plasmid pOJ325 is presented in FIG. 3 of the accompanying drawings. Because the ~14 kb, carG gene-containing BglII restriction fragment of plasmid pOJ171 could insert into plasmid pOJ160 in either of two orientations, the ligation also produced plasmid pOJ325A, which differs from plasmid pOJ325 only with respect to the orientation of the carG gene-containing restriction fragment.

The BamHI site on plasmid pOJ160 resides within a polylinker that itself forms part of the DNA sequence encoding the lacZ α-fragment. Expression of the lacZ α-fragment in an *E. coli* ΔM15 strain, such as *E. coli* K12 RR1ΔM15 (NRRL B-15440), restores the strain's ability to produce a functional µ-galactosidase enzyme. Thus, plasmid pOJ160 can restore µ-galactosidase activity to the *E. coli* K12 RR1ΔM15 strain. However, insertion of DNA into a restriction site of the polylinker on plasmid pOJ160, as occurs in the construction of plasmid pOJ325, disrupts the lacZ α-fragment coding sequence and concomitantly destroys the ability of the plasmid pOJ160 derivative to complement the ΔM15 mutation. β-galactosidase can hydrolyze X-Gal, which is 5-bromo-4-chloro-3-indolyl-β-D-galactopyranoside, chloro-3-indolyl-β-D-galactopyranoside, a colorless compound, to an indigo-colored product and thus allows for a convenient screening method for discriminating between transformants containing starting plasmid pOJ160 and those containing a plasmid pOJ160 derivative, such as plasmid pOJ325.

To prepare *E. coli* K12 RR1ΔM15 cells that are competent for transformation, the lyophils of *E. coli* K12 RR1ΔM15 obtained from the NRRL are reconstituted to isolate single colonies. One single-colony isolate of RR1ΔM15 was inoculated into 10 ml of L broth (10 g of Bacto-tryptone, 10 g of NaCl, and 5 g of Bacto-Yeast Extract per liter), and the culture was incubated at 37° C. overnight with aeration. The overnight culture was used to inoculate 200 ml of L broth to yield a culture with an O.D.$_{600}$ of about 0.1. The culture was incubated at 37° C. with aeration until the O.D.$_{600}$ was about 0.6. The culture was collected by centrifugation at 4000Xg for 10 minutes at 4° C., resuspended in 100 ml of cold 50 mM CaCl$_2$, and incubated on ice for 15 to 30 minutes.

The cells were again collected by centrifugation and resuspended in 10 ml of cold 50 mM CaCl$_2$ containing 20% glycerol. A 200 µg aliquot of the cells was added to the ligated DNA prepared above. The cell-DNA mixture was incubated on ice for one hour, centrifuged, and the cell pellet was resuspended into 0.5 ml of L broth in a 1.5 ml tube and incubated with aeration at 37° C. for one-half hour.

Figure 3:
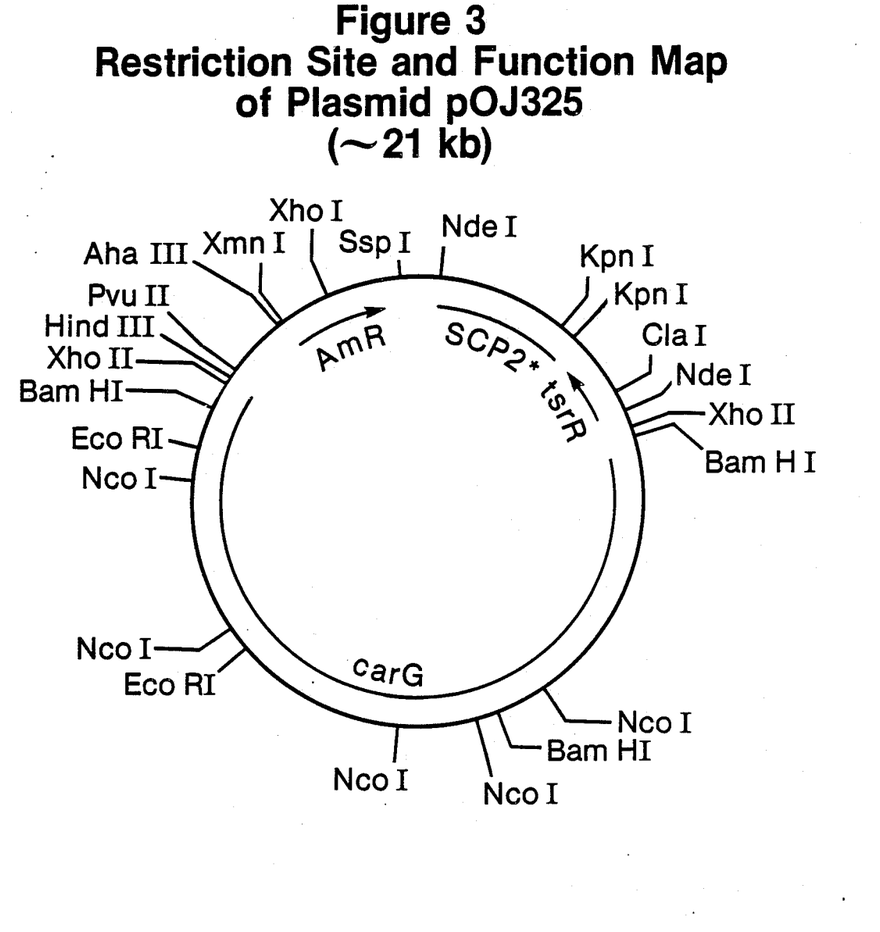
FIG. 3 is a restriction site and function map of plasmid pOJ325.

Aliquots of the transformation mixture were plated on L-agar (L-broth with 15 grams per liter agar) plates containing 200 µg apramycin/ml, 40 µg X-gal/ml, and 40 µg IPTG/ml. IPTG serves to derepress the lac promoter present on plasmid pOJ160. The plates were incubated at 37° C. overnight. Colonies that contain a plasmid without an insert, such as *E. coli* K12 RR1ΔM15/pOJ160, appear blue on these plates. Colonies that contain a plasmid with an insert, such as *E. coli* K12 RR1ΔM15/pOJ325, are white. Several apramycinresistant, white colonies were selected and then screened by restriction enzyme analysis of their plasmid DNA. As noted in the restriction site and function map of plasmid pOJ325, when a BamHI overlap is ligated to a BglII overlap, an XhoII site is created. Neither BamHI nor BglII, however, will cut the site resulting from joining a BamHI-cleaved fragment to a BglII-cleaved fragment. Two other BglII restriction fragments of ~14 kb were also generated from the BglII digestion of plasmid pOJ171 and could insert into the BamHI-digested plasmid pOJ160. Such unwanted vectors were differentiated from plasmid pOJ325 by digestion with restriction enzymes AhaIII and XbaI. These sites are present in portions of plasmid pOJ171 derived from plasmid pKC462A, and so are present in the undesired ~14 kb BglII restriction fragments of plasmid pOJ171, but are completely absent in the S. thermotolerans DNA insert portion of pOJ171, which contains the carG gene. Plasmid DNA was obtained from the E. coli K12 RR1ΔM15/pOJ325 transformants in accordance with the procedure for isolating plasmid pOJ160 DNA, described above. The plasmid pOJ325 DNA can be used to transform Streptomyces thermotolerans, as described in Example 3, below.

EXAMPLE 3

Transformation of Streptomyces thermotolerans (NRRL 15270) to Produce S. thermotolerans/pOJ171 and S. thermotolerans/POJ325

A. List of Solutions

The following solutions are referred to throughout the Examples and are presented here for clarity.

1. P Media (~100 ml):

| Ingredient | Amount |
| --- | --- |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25 M, pH = 7.2 | 10 ml |

2. Trace element solution (~1 L):

| Ingredient | Amount |
| --- | --- |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ | 1 L |

3. R2 Regeneration Media (~1 L):

| Ingredient | Amount |
| --- | --- |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |

The pH is adjusted to pH=7.2 before autoclaving. After autoclaving, add:

| | |
| --- | --- |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |

4. Soft Nutrient Agar (SNA, ~1 L):

| Ingredient | Amount |
| --- | --- |
| Difco Bacto Nutrient Broth | 8 g |
| Agar | 5 g |

5. R2YE medium is R2 medium with 20 ml of 25% yeast extract added per liter.

6. Yeast Extract - Malt Extract (YEME, ~1 L):

| Ingredient | Amount |
| --- | --- |
| Yeast extract | 3 g |
| Peptone | 5 g |
| Malt extract | 3 g |
| Glucose | 10 g |

7. YEME+34% Sucrose Liquid Complete Media is YEME with 340 g/L of sucrose.

8. YMX Media (~1 L):

| Ingredient | Amount |
| --- | --- |
| Yeast extract | 3 g |
| Malt extract | 3 g |
| Glucose | 2 g |
| Agar | 20 g |

9. YMX Agar is 0.3% yeast extract, 0.3% malt extract, 0.2% dextrose, and 2.0% agar.

10. CSI Media (~1 L):

| Ingredient | Amount |
| --- | --- |
| Soybean meal | 15 g |
| Casein | 1 g |
| Cerelose | 25 g |
| Blackstrap molasses | 3 g |
| $CaCO_3$ | 2.5 g |
| Czapek Mineral Stock | 2 ml |
| Water (deionized) | 1 L |
| pH adjusted to 7.2 prior to sterilization | |

18. Czapek's Mineral Mix (~1 L):

| | |
| --- | --- |
| KCl | 100 g |
| $MgSO_4.7H_2O$ | 100 g |
| Deionized Water | 900 ml |

$FeSO_4.7H_2O$ (2 g) was dissolved in 100 ml deionized water containing 2 ml of concentrated HCl. This solution was added to the above KCl/MgSO$_4$·7H$_2$O solution to complete preparation of the Czapek's Mineral Mix.

12. Bennett's Agar (~1L):

| Ingredient | Amount |
| --- | --- |
| Deionized H$_2$O | 1000 ml |
| Potato Dextrin | 10 g |
| N-Z Amine A | 2 g |
| Gibco bactoagar | 15 g |
| Gibco beef extract | 2 g |
| Yeast extract | 1 g |
| Czapek's mineral stock | 2 ml |

B. Transformation

Plasmid pOJ171 and plasmid pOJ325 were individually used to transform *Streptomyces thermotolerans* (NRRL 15270) in substantial accordance with the procedure set forth below.

*Streptomyces thermotolerans* (NRRL 15270) was plated on Bennett's agar and incubated at 30° C. for about 72 hours. A spore scraping was removed from the plate and used to inoculate 10 ml of TSB (TSB is made at 30 g/l and is obtained from Baltimore Biological Laboratories (BBL), P.O Box 243, Cockeysville, Md. 21031). The culture was incubated in an air-shaker incubator at 30° C. for ~30 hours. This culture was homogenized and sonicated; then, 3 ml of the culture were used to inoculate 17 ml of TSB containing 0.4% glycine. The culture was incubated in an air-shaker incubator at 30° C. for about ~24 hours. This culture was again homogenized and sonicated; then, 3 ml of the culture were used to inoculate 17 ml of TSB containing 0.4% glycine. The culture was incubated at 30° C. for about 16 hours. The culture was again homogenized and sonicated; then, the mycelial fragments were harvested and washed two times with a 10.3% sucrose solution. The mycelial fragments were resuspended in 20 ml of P media (Example 3Al) containing 1 mg/ml lysozyme, and the resulting solution was incubated at room temperature for about one to one-and-one-half hours. During this protoplasting step, the cells were pipetted up and down to disperse clumps. The protoplasts were collected and washed two times with P medium. The protoplasts were then suspended in 2 ml of P medium. This process usually generates about 2 to $5 \times 10^7$ protoplasts per 200 μg of solution.

Approximately 200 μg of the protoplast solution were used per transformation. About 1 μg of the transforming DNA, in 10 μl of either ligation or TE buffer, was added to 50 μl of a 1 mg/ml solution of heparin (Sigma Chemical Co, P.O. Box 14508, St. Louis, Mo. 63178) and mixed. The DNA solution was added to the protoplasts; then, about 0.9 ml of 55% polyethylene glycol 1000 (Sigma) in P media were added to and mixed with the protoplasts. The cell-DNA mixture was vortexed and then plated onto R2 medium (Example 3A3); each plate was inoculated with about 0.1 ml of cells mixed with ~3 ml of R2-modified soft agar (103 g sucrose, 0.5% agar 10.12 g MgCl$_2$, 2.22 g CaCl$_2$, and 5.72 g TES at pH=7.2 per liter). The plates were incubated at 30° C. overnight (~16 hours) and then overlaid with ~3 ml of R2-modified soft agar containing enough apramycin to give a final concentration, after diffusion, of 25 μg/ml. The plates were then incubated for about four days at 30° C., when colonies became visible to the unaided eye.

EXAMPLE 4

A. Plate-Plug Assay

*Streptomyces thermotolerans*(NRRL 15270)/pOJ325 transformants were patched from the R2-agar regeneration plates to plates containing Bennett's agar (Example 3A12) and 25 μg/ml apramycin and incubated at 37° C. for 2-3 days until the colonies were 5-10 millimeters in diameter. The colonies were then plugged and the plugs transferred, using a sterile transfer tube (Spectrum Medical Industrial, Inc., Los Angeles, Calif. 90054) to trypticase soy agar (TSA) plates, which had been previously overlayed with soft-agar nutrient broth (Difco Laboratories, Detroit, Mich. 48232) containing *Micrococcus luteus* X160 (ATCC. 9341). The plates were incubated at 37° C. for 16-24 hours. *Micrococcus luteus* (ATCC. 9341) is sensitive to carbomycin and resistant to apramycin. Consequently, this *M. luteus* strain cannot grow around a plug which contains Streptomyces that are producing carbomycin. In the plate-plug assay done with *S. thermotolerans* wild-type cells (ATCC. 11416), *S. thermotolerans*(NRRL 15270)/pOJ325, and *S. thermotolerans*(NRRL 15270)/pOJ171 there were clear zones of inhibition of *M. luteus* growth around the plugs. These zones, about 20 to 25 mM in size, of inhibition, which were absent around the *S. thermotolerans* NRRL 15270 plugs, indicated the transformants were producing carbomycin.

B. Bioautography

Several plugs were prepared from the plates containing Streptomyces thermotolerans(NRRL 15270)/pOJ325 used in Example 4A. These plugs were placed onto a thin-layer chromatography plate (Merck, P.O. Box 2000, Rahway, N.J. 07065, pre-coated silica gel #60 F-254) next to a sample of carbomycin standard. The plugs were left on the plate for a time sufficient for diffusion to occur; then, the plate was subjected to ascending liquid chromatography in 95:5:5 ethylacetate:days diethylamine:methanol. The developed chromatograms were dried thoroughly in a fume hood for at least two hours. The chromatograms were then placed face down on *Micrococcus luteus* X160-seeded TSA plates for ~15 minutes. The chromatograms were removed from the plates, and the plates were incubated at 37° for 16-24 hours.

The chromatograms for the plugs prepared from Streptomyces thermotolerans/pOJ325 transformants produced zones of inhibition resulting from substances on the chromatogram that comigrated with the carbomycin standard.

C. Fermentation

Cultures of *Streptomyces thermotolerans* ATCC 11416, *S. thermotolerans* NRRL 15270, and *S. thermotolerans*(NRRL 15270)/pOJ325 were grown on slants of Bennett's medium containing 25 μg/ml apramycin. These cultures were individually used to inoculate several 50 ml aliquots of vegetative medium. The medium contained 27.5 g of Trypticase Soy Broth per liter of deionized water.

Each 50 ml aliquot of inoculated medium was incubated in a 250 ml Erlenmeyer flask at 37° C. for 48 hours in an air-shaker incubator rotating through an arc of two inches at 260 rpm. Two ml aliquots of each vegetative culture were used to inoculate several 50 ml aliquots of CSI (3A10) fermentation medium. Each 50 ml aliquot of inoculated fermentation medium was incubated 48 hours in a 250 ml Erlenmeyer flask at 37° C. in an air-shaker incubator rotating through an arc of two inches at 260 rpm. Every 24 hours, 20 μl of each fermentation culture was removed and placed on assay discs (¼" Schleicher and Schuell Analytical Paper). After drying, these discs were placed on agar plates seeded with *Micrococcus luteus*. The plates were then incubated at 37° C. for 16 hours. Zones of inhibition were measured and recorded.

After 48 hours of fermentation, 400 ml of whole broth from each culture were adjusted to a pH of 8.5 with 1N NaOH and extracted three times with ethyl acetate. The ethyl acetate portion of the resulting suspension was removed and concentrated to dryness on a Rotavapor-EL (Buchi). The crude, dried preparation was suspended in methanol and analyzed by reverse-phase HPLC., using a Rainin Dynamax 150-C8 column (4.5×350 mm). Carbomycin was assayed using 55% acetonitrile/water/sodium perchlorate (0.1M and pH=2.3) at a flow rate of 2 ml/min. Carbomycin was detected by UV absorption at 239 nm. Quantitation was determined using a carbomycin (Pfizer) standard at 2 mg/ml.

As measured by HPLC., *Streptomyces thermotolerans*(NRRL 15270)/pOJ325 makes 4.8 times as much carbomycin as *S. thermotolerans* ATCC. 11416. *S. thermotolerans* NRRL 15270 makes no carbomycin. As measured by antimicrobial activity, strain *Streptomyces thermotolerans*(NRRL 15270)/pOJ325 produces more antibiotic than either *S. thermotolerans* ATCC. 11416 or *S. thermotolerans* NRRL 15270.

TABLE VII

| Strain | Media | HPLC Assay |
| --- | --- | --- |
| *S. thermotolerans* ATCC 11416 | CSI | 1.85 μg/ml in whole broth |
| *S. thermotolerans* (NRRL 15270)/pOJ325 | CSI | 8.95 μg/ml in whole broth |

| | Zone Size-CSI Medium (X186 Activity) | |
| --- | --- | --- |
| Strain | 24 hr. | 48 hr. |
| *S. thermotolerans* ATCC 11416 | 21 mm | 22 mm |
| *S. thermotolerans* (NRRL 15270)/pOJ325 | 29 mm | 29 mm |
| *S. thermotolerans* NRRL 15270 | 0 mm | 0 mm |

We claim:

1. A method for increasing the carbomycin-producing ability of an organism that comprises (1) transforming said organism with a recombinant DNA vector that codes for expression of the carG activity; and (2) culturing said organism transformed in step (1) under conditions that allow the production of carbomycin.

2. The method of claim 1, wherein said organism is *Streptomyces thermotolerans*.

3. The method of claim 1, wherein said organism is *Streptomyces thermotolerans* ATCC. 11416.

4. The method of claim 1, wherein said carbomycin-producing organism is *Streptomyces thermotolerans* NRRL 15270.

5. The method of claim 1 wherein said recombinant DNA vector is plasmid pOJ171.

6. The method of claim 1 wherein said recombinant DNA vector is plasmid pOJ325.

7. The method of claim 3 wherein said recombinant DNA vector is plasmid pOJ171.

8. The method of claim 3 wherein said recombinant DNA vector is plasmid pOJ325.

9. The method of claim 4 wherein said recombinant DNA vector is plasmid pOJ171.

10. The method of claim 4 wherein said recombinant DNA vector is plasmid pOJ325.

11. A recombinant DNA molecule that comprises the carG activity of *Streptomyces thermotolerans*.

12. The DNA molecule of claim 11 that is the ~14 kb BglII restriction fragment of plasmid pOJ171.

13. The DNA molecule of claim 11 that is a recombinant DNA vector.

14. The vector of claim 13 that is a plasmid.

15. The plasmid of claim 14 that is plasmid pOJ171.

16. The plasmid of claim 14 that is plasmid pOJ325.

17. A recombinant DNA host-cell transformed with a vector that comprises the carG gene of a streptomyces thermotolerans.

18. The recombinant DNA host cell of claim 17 selected from the group consisting of *E. coli* and Streptomyces.

19. The recombinant DNA host cell of claim 18 that is *Streptomyces thermotolerans*.

20. The recombinant DNA host cell of claim 18 that is *E. coli* K12 SF8/pOJ171.

21. The recombinant DNA host cell of claim 18 that is Streptomyces thermotolerans (NRRL 15270)/pOJ171.

22. The recombinant DNA host cell of claim 18 that is Streptomyces thermotolerans (NRRL 15270)/pOJ325.

23. An isolated DNA molecule from Streptomyces that encodes carG activity, said DNA molecule capable of hybridization with the DNA molecule of claim 11, or a portion thereof.

* * * * *

UNITED STATES PATENT AND TRADEMARK OFFICE
CERTIFICATE OF CORRECTION

PATENT NO. : 4,952,502

DATED : August 28, 1990

INVENTOR(S) : Janet K. Epp and Brigitte E. Schoner

It is certified that error appears in the above-identified patent and that said Letters Patent is hereby corrected as shown below:

Column 17:
 In Claim 1, line 55, please delete "an" and add therefor
 -- a Streptomycetes --.

In Claim 1, line 3, please delete "that comprises" and add therefor
 -- , said method comprising the steps of: --.

In Claim 1, line 5, please delete "; and" and add therefor
 -- of Streptomyces thermotolerans; and --.

Column 18:
 In Claim 17, 36 & 37, please delete "of a streptomyces thermotolerans".

Signed and Sealed this

Twelfth Day of May, 1992

*Attest:*

DOUGLAS B. COMER

*Attesting Officer*   *Acting Commissioner of Patents and Trademarks*